United States Patent [19]

Anthony

[11] Patent Number: 5,639,955
[45] Date of Patent: Jun. 17, 1997

[54] SYSTEM FOR AUTOMATED CALIBRATION OF SENSORS

[75] Inventor: William S. Anthony, Greenville, Miss.

[73] Assignee: The United States of America as represented by the Secretary of Agriculture, Washington, D.C.

[21] Appl. No.: 598,418

[22] Filed: Feb. 8, 1996

[51] Int. Cl.⁶ .................. G01N 21/89; G01N 33/00; G01N 33/36
[52] U.S. Cl. .................. 73/1.01; 73/866.5; 250/252.1; 250/576; 356/243; 356/245; 356/421
[58] Field of Search .................. 73/1 R, 866.5, 73/864.31, 863.54, 863.44; 250/252.1 R, 252.1 A, 573, 576; 356/36, 243, 244, 245, 408, 421, 422, 423, 445, 229

[56] References Cited

U.S. PATENT DOCUMENTS

| | | | |
|---|---|---|---|
| 3,869,213 | 3/1975 | Greene | 356/244 |
| 4,154,533 | 5/1979 | Levine | 250/574 X |
| 4,464,054 | 8/1984 | Karras et al. | 250/226 X |
| 4,917,495 | 4/1990 | Steenhoek | 356/405 X |
| 5,087,120 | 2/1992 | Anthony | 250/576 X |
| 5,514,973 | 5/1996 | Byler et al. | 324/695 |
| 5,537,202 | 7/1996 | Komatsu et al. | 73/864.31 |
| 5,544,090 | 8/1996 | Stofner et al. | 356/430 |

*Primary Examiner*—Thomas P. Noland
*Attorney, Agent, or Firm*—M. Howard Silverstein; Joseph A. Lipovsky; John D. Fado

[57] ABSTRACT

A system for calibrating sensors used in analyzing agricultural solids which includes a calibration paddle possessing one or more calibration tiles for calibrating sensors used in analysis of agricultural solids and a rotary actuator for reversible translation of said calibration paddle between a dormant location which does not interfere with material flow or sample analysis, and an active location containing a calibration position suitable for sensor calibration.

19 Claims, 6 Drawing Sheets

5,639,955

SYSTEM FOR AUTOMATED CALIBRATION OF SENSORS

BACKGROUND OF THE INVENTION

1. Field of the Invention

The present invention relates generally to systems for grading or analyzing agricultural solids, such as cotton. More particularly, the present invention relates to an automated calibration system for sensors that are used for analyzing and grading agricultural solids.

2. Related Art

Cotton and other agricultural solids are officially classified and graded by the United States Department of Agriculture (USDA) Agricultural Marketing Service (AMS), as well as other organizations. This is accomplished by the measurement of numerous properties of the cotton such as color and trash content. A camera-type sensor is typically used to measure the color of the cotton, as well its trash content. Some organizations further utilize a separate moisture sensor, such as an infrared moisture sensor, to measure moisture content. These same sensors may also be used in a gin to monitor the properties of the cotton as it is being processed.

Industry protocol for measurement of cotton color and trash in a typical gin processing system requires verification of sensor calibration, and recalibration if necessary, after approximately every four hours of operation. Calibration has heretofore been done manually, using five different color reference tiles and one trash reference tile. In this process, five color reference tiles are sequentially placed in the viewing position for the color/trash camera sensor, with measurements from the color sensors then being taken and recorded for each individual tile. The gathered measurements are then used to calculate coefficients that optimally correlate the measured values with known color reference values. Similarly, a singular trash reference tile, with a known percentage of surface area occupied by dark spots, is manually placed in the viewing position for the color/trash camera sensor. Upon its measurement by the trash sensor an iterative process is used to calculate coefficients that optimally correlate the measured values with known trash content reference values.

Because cotton cannot be graded or analyzed during the sensor calibration process, the calibration process results in downtime for its processing. Presently calibration is a manual operation which is inefficient due to its being time and labor intensive. Therefore, there is a need in the art for a calibration system that can quickly and repeatably calibrate sensors without requiring continuous operator intervention.

SUMMARY OF THE INVENTION

The present invention provides a system for calibrating sensors that are used in analyzing agricultural solids. The system includes a calibration device that is reversibly movable between active calibration and dormant positions. A calibration paddle is provided that includes one or more tiles for calibrating a sensor system used in the sample analysis of agricultural solids. Moving means reversibly translate the calibration paddle between a dormant position which does not interfere with ongoing sample analysis by sensors, and an active position suitable for sensor calibration. The sampling device may be optionally utilized to complete the movement of the calibration paddle to the active location.

The calibration paddle may be reversibly moved between its dormant and active positions by means of a shaft, to which it is coupled, which in turn is coupled to a means for effecting lateral movement such as gearing or a single or multi-step cylinder actuated by any conventional means such as air or hydraulics. In an alternate embodiment the shaft may be slidably received within a second shaft that is in turn coupled to a rotary actuator which is capable of moving the second shaft and hence the calibration paddle in an arcuate pathway between the dormant and active positions. A means for effecting lateral movement such as gearing or a single or multi-step cylinder actuated by any conventional means then moves the calibration paddle laterally for the calibration of subsequent tiles.

The calibration paddle may include one or more color reference tiles, trash reference tiles, and/or moisture reference tiles. Control means, such as a programmable controller or a computer, may be used to direct movement of the calibration paddle and sampling device.

FEATURES AN ADVANTAGES

A feature of the present invention is that it can be used in conjunction with existing sampling devices of agricultural solids which allows its ready incorporation into existing gin processing systems.

Another advantage of the present invention is that system calibration can be done with no downtime from grading and analyzing.

A further advantage of the present invention is that with the enhanced speed, calibrations can be done more often without adversely affecting material flow through a gin processing system. With the instant invention calibrations can be done at intervals as frequent as once per minute (preferably once per hour), rather than the art standard of once every four hours of operation.

It is yet a further advantage of the present invention that it provides repeatable calibrations with a greater control of accuracy. A further advantage is that the system can provide notification should operator intervention be required, such as when either sensor or calibration means fail.

A still further advantage of the present invention is that the same calibration system is capable of being used in both official grading and commercial gin processing systems.

BRIEF DESCRIPTION OF THE DRAWINGS

The present invention is described with reference to the accompanying drawings. In the drawings, like reference numbers indicate identical or functionally similar elements. Additionally, the left-most digit of a reference number identifies the drawing in which the reference number first appears.

DETAILED DESCRIPTION OF THE EMBODIMENTS

I. Overview

The present invention provides a system for automated calibration of a color and trash camera or video sensor, as well as a moisture sensor, that are used in systems for analyzing and grading agricultural solids, such as cotton. A calibration paddle is provided that includes one or more tiles useful for calibrating sensors for properties including color, trash content and moisture content. The calibration paddle is moved between a dormant location and an active location. In the dormant location, the calibration paddle is situated for non-interference with ongoing sample analysis of the agricultural solid. In the active location, the calibration paddle is situated for recalibration of the sensors.

The active location of the calibration paddle includes a calibration position. Once moved to the active location, the calibration paddle is further positioned within the active location to place a specific calibration tile at the calibration position. Once recalibration, through use of established protocol, of a particular calibration tile is complete, the paddle is repositioned within the active location to align the next calibration tile for use in the recalibration process. In this manner, recalibration of one or more sensors can be accomplished through movement of the paddle to align the requisite calibration tiles. Once recalibration is complete, the calibration paddle is returned to its dormant location.

II. System Description

Figure 1:
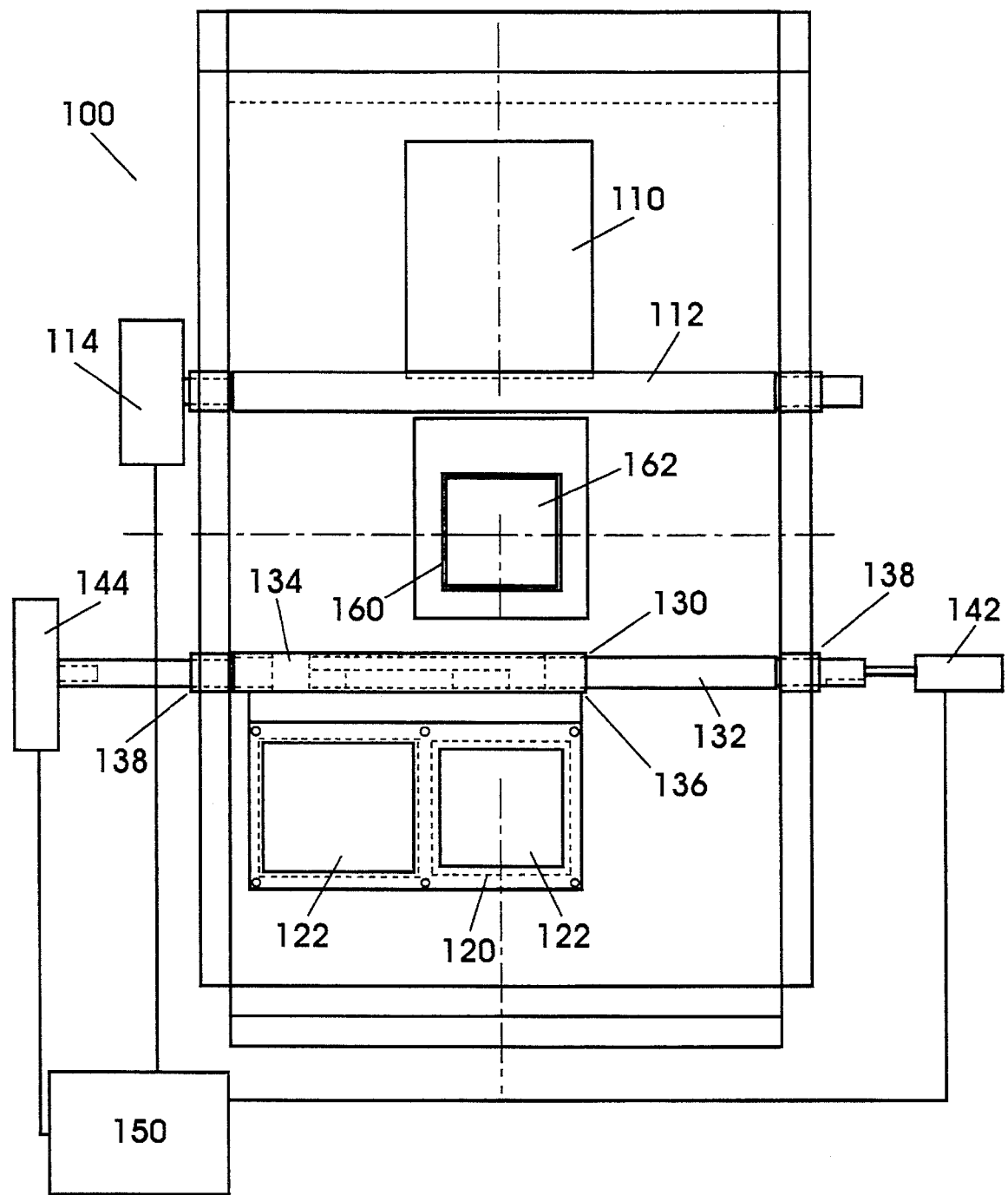
FIG. 1 shows a front view of an embodiment of a calibration system of the present invention.

In FIG. 1, one embodiment of the calibration system of the present invention is shown generally at 100. While the orientation of the calibration system shown in FIG. 1, is vertical, it is to be understood that any other orientation can also be used. System 100 includes a calibration paddle 120 that includes one or more calibration tiles 122. Although two calibration tiles 122 are shown in FIG. 1, any number of calibration tiles may be used. Calibration tiles suitable for use with the present invention include, but are not limited to, color reference tiles, trash reference tiles, and moisture reference tiles.

Paddle 120 is coupled to an inner shaft 132, such as by welding. Inner shaft 132 is slidably disposed within an outer shaft 134. Inner shaft 132 and outer shaft 134 form concentric shafts, shown generally at 130. A rotary actuator 144 is used for rotating outer shaft 134. Inner shaft 132 is coupled to a means for effecting lateral movement such as cylinder 142, actuated by any conventional means such as air or hydraulics or, in the alternative, gearing. Air cylinder 142 slides inner shaft 132 within outer shaft 134. A nylon bearing 136 provides a means to enhance lateral and rotary movements as well as to prevent galling. Likewise, a linear steel ball bearing 138 is used to enhance lateral and rotary movement without undue friction. It is to be understood that bearings 134 and 138 may be substituted by any art equivalent type of friction reducing device.

Figure 3:
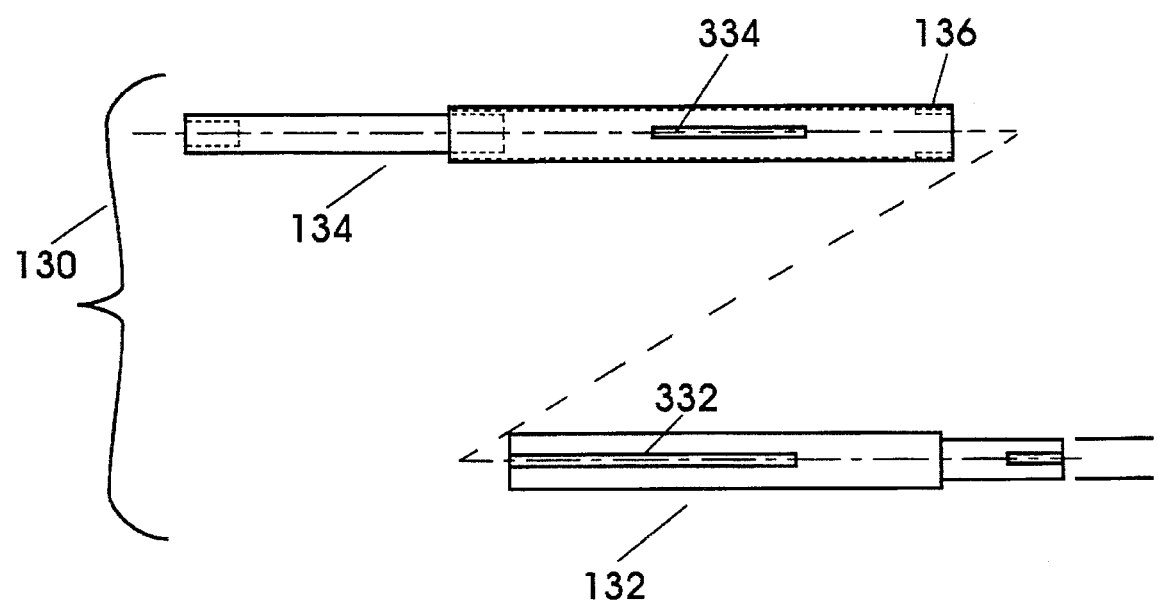
FIG. 3 shows an expanded view of the concentric shafts shown in FIG. 1.

FIG. 3 shows an expanded view of concentric shafts 130. Inner shaft 132 is machined to fit into outer shaft 134. A slot 334 is provided in outer shaft 134, and a slot 332 is provided in inner shaft 132. Slots 334 and 332 enable calibration paddle 120 to be coupled to inner shaft 132 and slide within outer shaft 134. Alternatively, calibration paddle 120 could be coupled to outer shaft 134. In such a configuration, outer shaft 134 is moved laterally with respect to inner shaft 132 which is held in a fixed position. This alternate configuration eliminates the need for the grooves or slots in the shafts, thereby reducing opportunity for contamination of the calibration tiles. Nylon bearing 136 and steel bearing 138 are used at the juncture of the two shafts to enhance freedom of movement and to prevent galling.

System 100 also includes a sampling device, such as a paddle sampler 110 which is coupled to a shaft 112. A rotary actuator 114 is used for rotating shaft 112. Paddle sampler 110 will be further described below with respect to FIGS. 5–7.

Rotary actuators 114 and 144 are preferably a Speedaire model 2A124 or Schraeder model PTR-251-0902DP-AB24M-CSXX. Means for effecting lateral movement of shaft 112 is preferably cylinder 142 which in turn is preferably a Speedaire model 6X374.

A calibration position, which may correspond to the location of a sensor needing calibration, is shown generally at 160 in FIG. 1. A lens or window 162 is provided at calibration position 160 to physically isolate sensors from direct contact with the agricultural material and thus prevent their contamination thereby. Lens or window 162 is constructed of material that does not interfere with the taking of sensor readings and the recalibration process.

A control means 150, coupled to rotary actuators 114 and 144, and cylinder 142 through, for example, solid-state relays mounted on a relay card, is provided for controlling movement of paddle sampler 110 and calibration paddle 120. Control means 150 may further be in the form of a programmable controller or a conventional desktop or personal computer, such as an IBM PC or the like, which typically includes a processor, display, keyboard and memory storage.

Control means 150 may also be used to initiate calibration measurement by the sensors and to process calibration measurement data. In another embodiment control means 150 may be further configured to repeat the calibration protocol and/or provide operator notification should calibration readings fall outside of predetermined limits; as might occur when a faulty or damaged calibration tile is being used. Operator notification can be in any form, such as visual or auditory alarms, that indicate the need for manual intervention.

Figure 2:
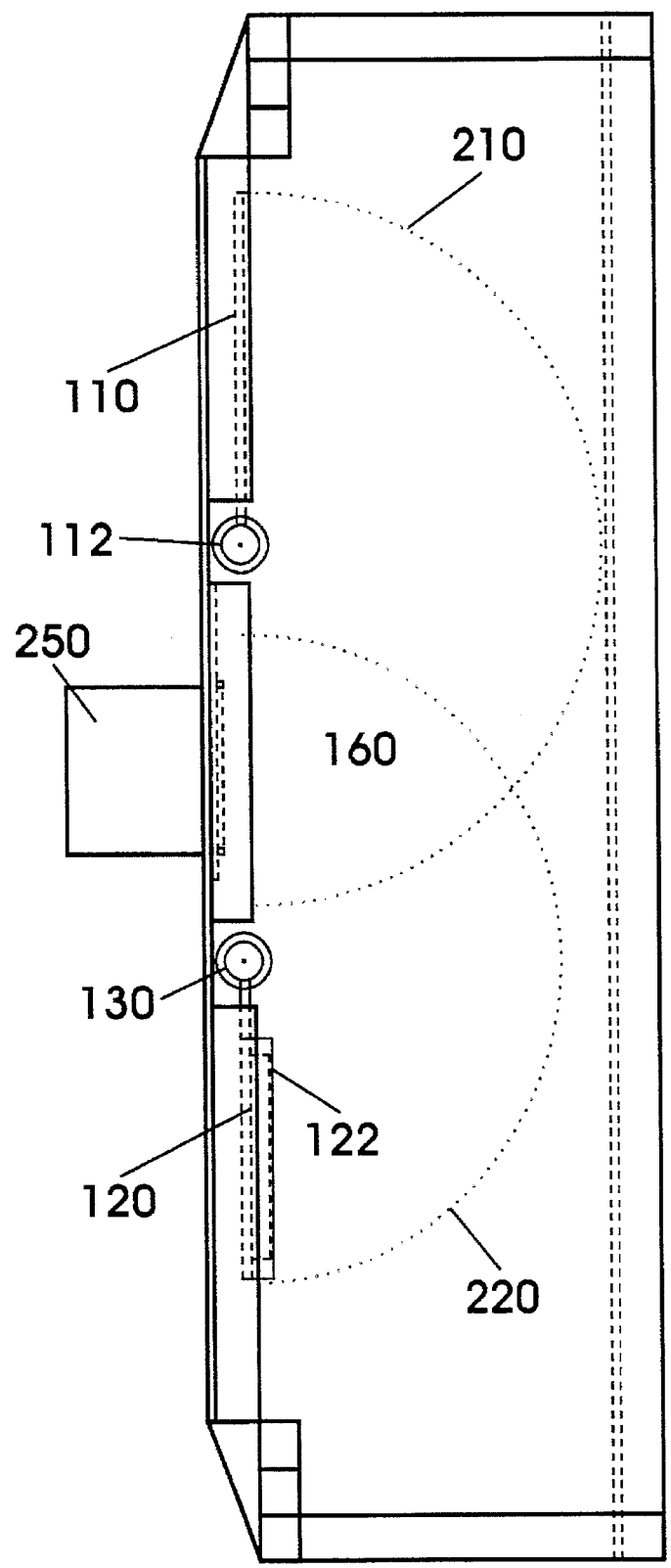
FIG. 2 shows a side view of the calibration system shown in FIG. 1.

In FIG. 1, calibration paddle 120 is shown in the dormant location. To move calibration paddle 120 from the dormant location to the active location, rotary actuator 144 rotates outer shaft 134 thereby rotating calibration paddle 120, attached thereto, in an arcuate pathway 120 (as seen in FIG. 2).

FIG. 1 further shows paddle sampler 110 in the retracted position. To move paddle sampler 110 from the retracted position to the pressing position, rotary actuator 114 rotates shaft 112 thereby rotating paddle sampler 110, attached thereto in an arcuate pathway 210 (as seen in FIG. 2).

Paddle sampler 110 may be used to complete movement of calibration paddle 120 from the dormant location to the active location. This may be done to reduce the potential for damage to either the calibration tiles 122 or lens 162 due to the use of excessive force at contact. In this embodiment the rotary actuator is used to move the calibration paddle from its dormant location through approximately 175° stopping just short of contact with lens 162, which would occur upon completion of 180° of travel. Paddle sampler 110 is then activated to move from the retracted position to the pressing position, which in doing so completes the movement of calibration paddle 120 to the active location by slowly pressing calibration paddle 120 against lens 162. Paddle sampler 110 can thus be used to complete the last approximately 5° of movement of calibration paddle 120 from the dormant location to the active location.

Once calibration paddle 120 is in the active location, calibration of the sensor corresponding to the specific calibration tile 122 aligned with calibration position 160 is carried out. Paddle sampler 110 is then returned to the retracted position and a means for effecting lateral movement such as cylinder 142 is then used to position a different calibration tile 122 at calibration position 160. Paddle sampler 110 is then activated to move from the retracted position to the pressing position to again slowly press calibration paddle 120 against lens 162. Calibration of the sensor corresponding to the calibration tile at calibration position 160 is carried out. This process is repeated until calibration of all desired tiles is complete, at which time calibration paddle 120 is returned to the dormant location.

A preferred embodiment alternative to the use of the paddle sampler would be the use of a rotary actuator that causes the calibration paddle to move through the full 180° of travel but is dampened for its approximately final 5° of motion so as to preclude the potential for damage to either the calibration tiles 122 or lens 162 due to the use of excessive force during contact. This same result could likewise be accomplished by the placement of a flange of force dampening material on calibration paddle 120 and/or lens 162.

Figure 4:
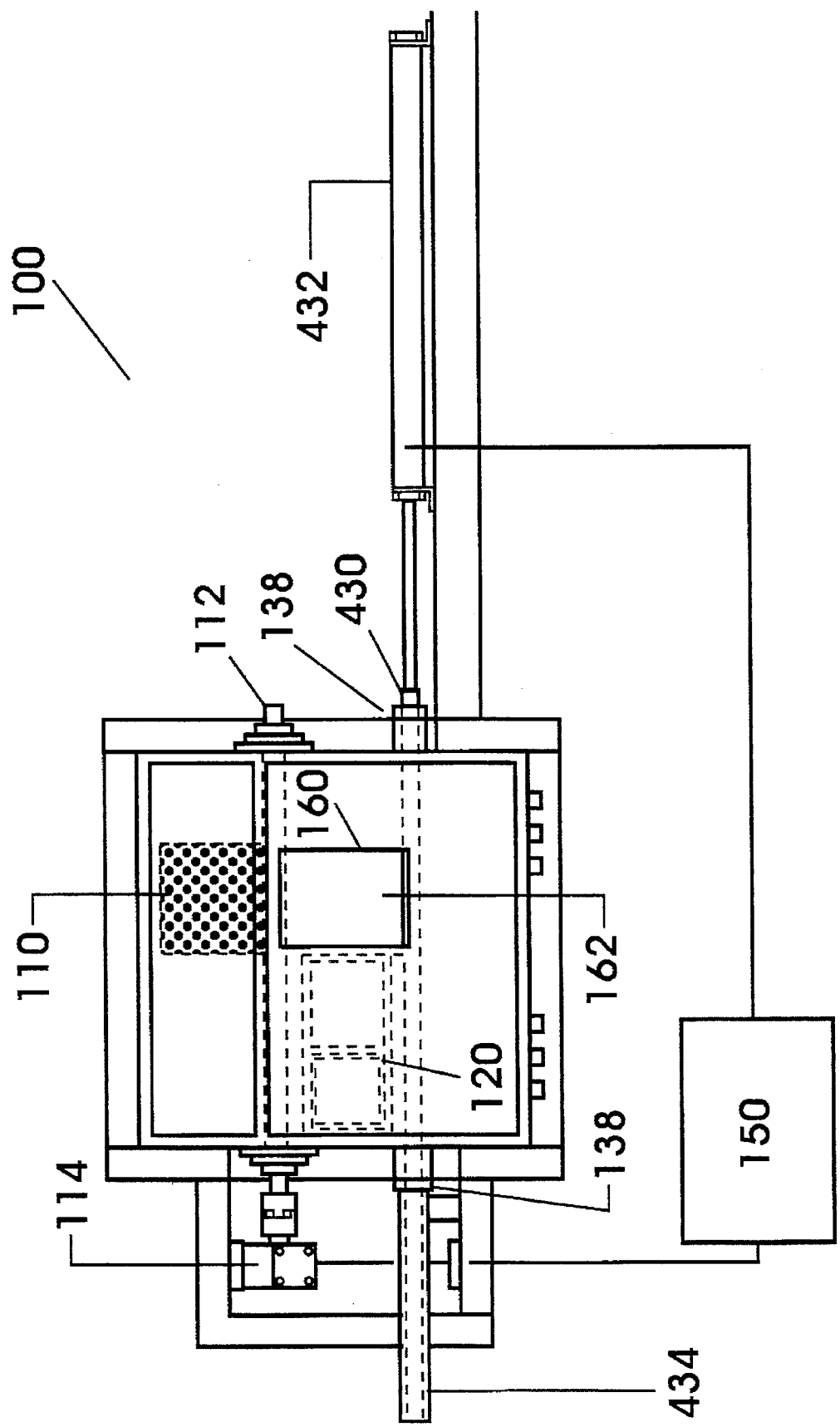
FIG. 4 shows a front view of an alternate embodiment of a calibration system of the present invention.

An alternate embodiment of the present invention is shown in FIG. 4 wherein calibration paddle 120 is slid laterally between the dormant and active locations by means of shaft 430 coupled to a means for effecting lateral movement such as cylinder 432, actuated by any conventional means such as air or hydraulics or, in the alternative, gearing. Cylinder 432 preferably possesses a multiple stroke, multiple position operation; with a two-stroke, two-position air cylinder such as Schraeder models 2.00 DXPSRMBY×5.125 and 2.00 DXPSRMBY ×12.5 being particularly preferred. Linear bearings 138 and box steel tube 434 are used to enhance movement of shaft 430 and to protect it during so, respectively.

Calibration tiles 122 are mounted on calibration paddle 120 so that they occupy a plane parallel to that of lens 162; in one embodiment, wherein the paddle sampler is used to contact the calibration tile against the lens, a clearance of approximately 3/16" between planes is provided so as to prevent deleterious contact between the calibration tiles 122 and lens 162 during movement of said tiles. In an alternate and preferred embodiment use of the paddle sampler is eliminated by having a juxtaposition of the calibration paddle and lens planes, wherein the tiles are in sliding contact with the lens wall. Deleterious effects due to contact between the calibration tiles and lens is ameliorated by coating the wall surface with a friction abating material such as Teflon™.

FIG. 4 shows calibration paddle 120 in the dormant location. To move calibration paddle to the active location, a means for effecting lateral movement such as cylinder 432 moves shaft 430 so that one of the calibration tiles is aligned with calibration position 160. In one embodiment of the invention paddle sampler 110 is then activated to move from the retracted position (shown in FIG. 4) to the pressing position. In a manner similar to that explained above with respect to the embodiment of FIGS. 1–3, paddle sampler 110 completes movement of calibration paddle 120 to the active location by slowly pressing calibration paddle 120 against lens 162.

Once calibration paddle 120 is in the active location, calibration of the sensor corresponding to calibration tile 122 aligned with calibration position 160 is carried out. Paddle sampler 110 is then returned to the retracted position. Means for effecting lateral movement of shaft 112 such as cylinder 432 is then used to position a different calibration tile 122 at calibration position 160. Paddle sampler 110 is then activated to move from the retracted position to the pressing position to again slowly press calibration paddle 120 against lens 162. Calibration of the sensor corresponding to the calibration tile at calibration position 160 is carried out. This process is continued until calibration is complete whereupon means for effecting lateral movement of shaft 112 such as cylinder 432 then returns calibration paddle 120 to the dormant location.

In a preferred embodiment, a tile cleaning means is utilized to prevent the buildup of contaminating material that can adversely affect the accuracy of the calibration process. One such means would be the utilization of a transversely fixed housing covered with a material such as felt, lamb's wool or cloth that is in spring-loaded contact with calibration paddle 120. The cleaning means would wipe calibration tiles 122 clean of debris when such are transversely moved across the path of said housing in the process of their being deployed and removed from the calibration position.

Alternate embodiments for contacting the calibration tiles 122 of the laterally actuated calibration paddle 120 to lens 162 include the use of a rotary actuator.

As shown in FIG. 4, control means 150 coupled to rotary actuator 114 and means for lateral movement of shaft 112 such as cylinder 432 through, for example, solid-state relays mounted on a relay card is used to control movement of paddle sampler 110 and calibration paddle 120.

Figure 5:
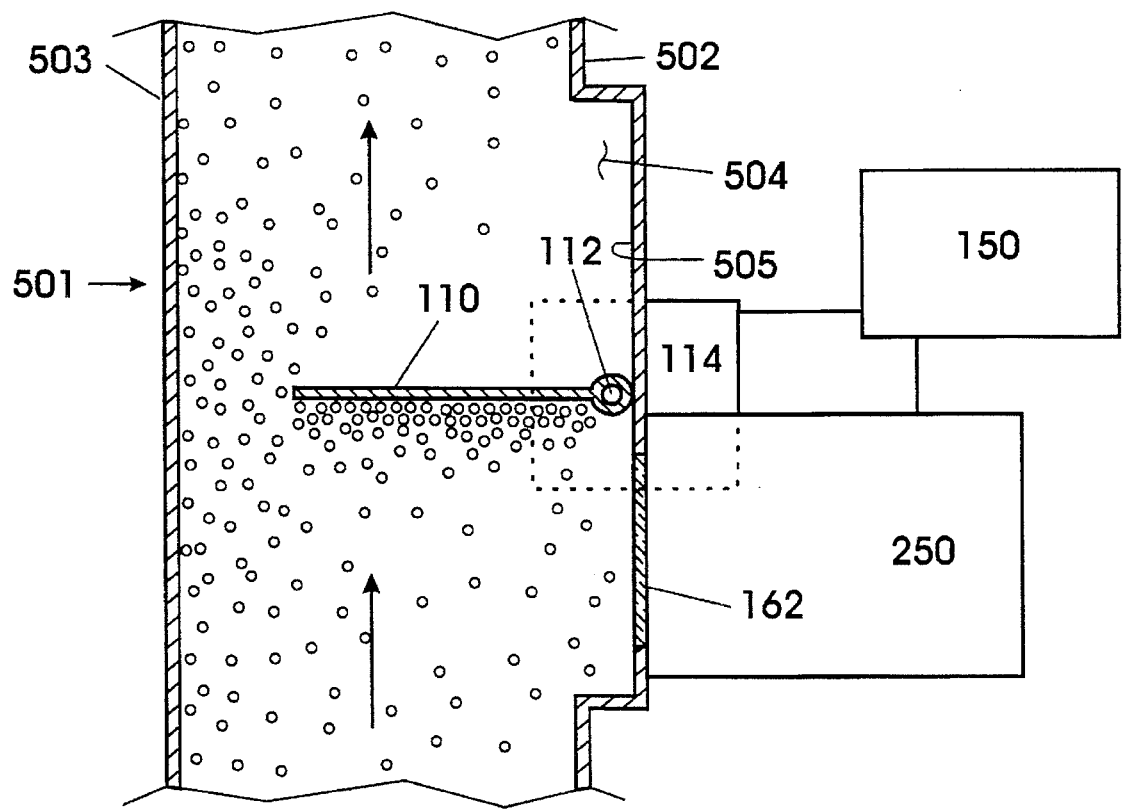
FIG. 5 shows an embodiment of a sampling device suitable for use in the calibration system of the present invention. The sampling device is shown in a solids-capturing position.

FIG. 5 shows an embodiment of a sampling device suitable for use in the calibration system of the present invention. Such a sampling device is described in U.S. Pat. No. 5,087,120, the entirety of which is incorporated herein by reference. This patent is directed to an apparatus that operates within the material flowstreams of cotton processing plants for the purpose of providing samples that present a face of uniform cotton density against a measuring surface used to analyze for properties such as color, trash content, and moisture content. FIG. 5 shows paddle sampler 110 installed in a ginning system. Reference numeral 510 designates a typical rectangular duct in a ginning system, wherein the cotton is traveling upwardly toward, for example, a lint cleaner. The cotton usually is moving rapidly at speeds of about 1000–5000 feet per minute, typically about 1500 feet per minute for lint cotton, and about 4500 feet per minute for seed cotton.

Reference numerals 502 and 503 designate the front and back walls, respectively, of duct 501. The distance therebetween, or duct depth, typically is about 4–8 inches in the case of a lint duct; while full scale width typically is about 48–96 inches. For seed cotton, round ducts, having a diameter of about 12–24 inches, normally are used.

Figure 6:
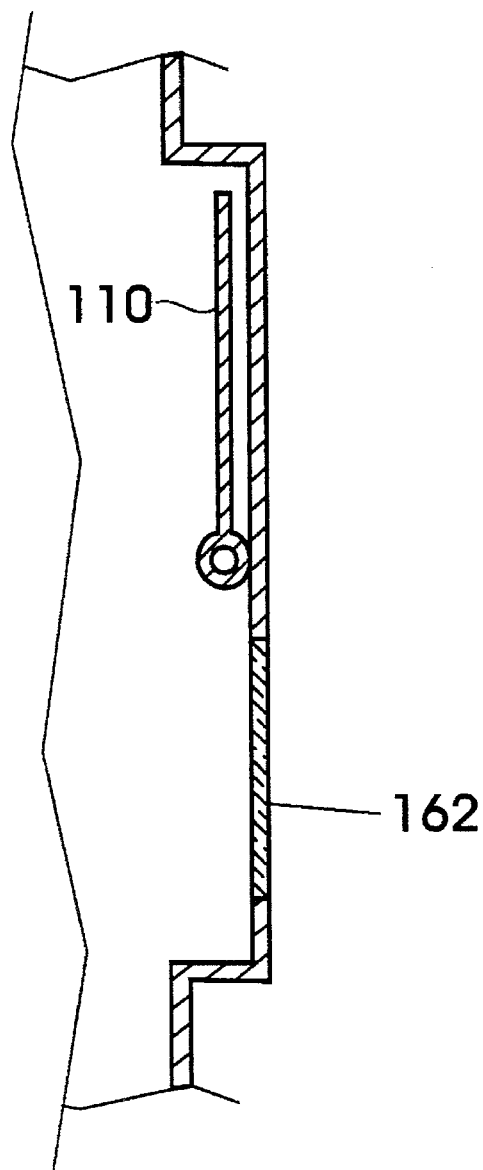
FIG. 6 shows the sampling device of FIG. 5 in a retracted position.
Figure 7:
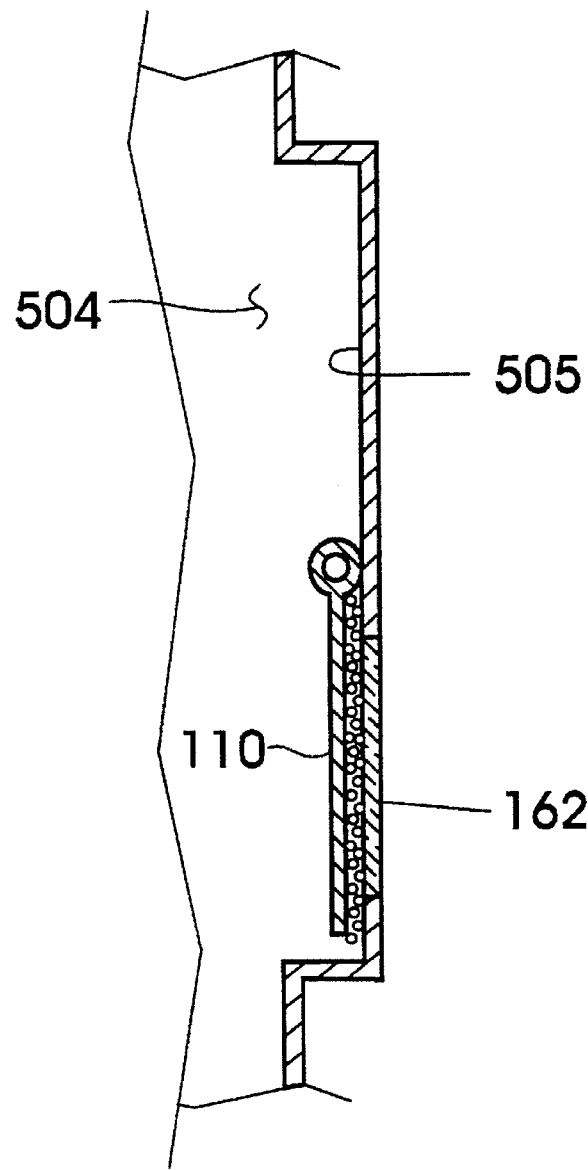
FIG. 7 shows the sampling device of FIG. 5 in a pressing position.

Provided in wall 502 is a recess 504. Positioned within recess 504 is shaft 112 driven by rotary actuator 114. Paddle sampler 110 is positioned in its solids-capturing or -halting mode in FIG. 5, i.e., the paddle projects transversely into the duct. FIGS. 6 and 7 illustrate the retracted and pressing positions, respectively, of paddle sampler 110. In the pressing and retracted positions, paddle sampler 110 is positioned totally within recess 504 so as not to cause flow obstruction to cotton passing through the duct.

Lens 162 is positioned in a surface 505 of wall 502. Analyzing means 250 is located adjacent lens and can include a color/trash camera-type sensor, such as the "Color/Trash Meter" made by Motion Control, Inc., Dallas, Tex. (now owned by Zellweger Uster, Knoxville, Tenn.), or a similar device made by Spinlab, Inc. (now owned by Zellweger Uster, Knoxville, Tenn.). Analyzing means 250 can also include an infrared moisture sensor, such as those made by Infrared Engineering Inc., Waltham, Mass., or Moisture Systems Inc., Hopkinton, N.J.

As shown in FIG. 5, analyzing means 250 can be coupled to control means 150. In this manner, control means 150 may be used to control the calibration process, including movement of paddle sampler movement of calibration paddle 120, as well as triggering the sensors to take the calibration measurements, and receiving and processing the calibration measurement data.

In operation, a computer, such as control means 150, can be used to control the calibration process using the system of the present invention. The computer returns the sampling device, such as paddle sampler 110, to the retracted position. The computer may use position sensors (not shown) to verify that the sampling device is in the retracted position. The computer then moves the calibration paddle from the dormant location to the active location. This positions a calibration tile, such as a color reference tile, at the calibration position. The sampling device can then activated to move from the retracted position to the pressing position to compress the calibration paddle against the lens or window so that calibration measurements for the first calibration tile can be made.

Once the calibration measurements for the first calibration tile are complete, the sampling device, if utilized, is returned to the retracted position. The calibration paddle is then moved to align a second calibration tile at the calibration position and the sampling device is again activated to move from the retracted position to the pressing position. This compresses the calibration paddle against the lens so that calibration measurements for the second calibration tile can be made. This process is repeated for all of the calibration tiles. Once the calibration process is complete, the calibration paddle is returned to the dormant location. Analyzing or grading samples of the agricultural solids can then continue, without any interference from the calibration paddle.

While various embodiments of the present invention have been described above, it should be understood that they have been presented by way of example only, and not limitation. For example, the invention may be used in conjunction with other sensors used in analyzing agricultural solids, or in other types of systems requiring calibration of sensors. Thus, the breadth and scope of the present invention should not be limited by any of the above-described exemplary embodiments, but should be defined only in accordance with the following claims and their equivalents.

What is claimed is:

1. A calibration system for use in analyzing agricultural solids, comprising:

a calibration paddle possessing one or more tiles for calibration of sensors used for analyzing the agricultural solid; and moving means for reversible translation of said calibration paddle between a dormant location which does not interfere with material flow or sample analysis, and an active location containing a calibration position suitable for sensor calibration.

2. The calibration system of claim 1, further comprising:

positioning means for lateral placement of said calibration paddle within the active location to thereby position a specific calibration tile at the calibration position.

3. The calibration system of claim 2, wherein said positioning means comprises:

a laterally movable shaft to which said calibration paddle is coupled; wherein said shaft is actuated by a means for effecting its lateral movement.

4. The calibration system of claim 3, wherein said means for effecting lateral movement of said shaft is a cylinder.

5. The calibration system of claim 4, wherein said calibration paddle comprises:

two to six calibration tiles, and wherein said cylinder moves said shaft to sequentially position each calibration tile at its respective calibration location.

6. The calibration system of claim 3, wherein said moving means further comprises:

a second shaft, within which said first shaft is slidably received; and a rotary actuator coupled to said second shaft capable of rotating said second shaft to thereby rotate said calibration paddle in an arcuate pathway between said dormant and active locations.

7. The calibration system of claim 2, further comprising:

control means coupled to said moving means and to said positioning means for controlling movement of said calibration paddle.

8. The calibration system of claim 10, further comprising:

a rotary actuator for moving said sampling device between the retracted position and the pressing position, wherein said control means is coupled to said rotary actuator for controlling movement of said sampling device.

9. The calibration system of claim 1, further comprising:

a sampling device reversibly movable between retracted and pressing positions, wherein movement of said sampling device to the pressing position completes movement of said calibration paddle to the active location.

10. The calibration system of claim 9, further comprising:

a rotary actuator for moving said sampling device between the retracted and pressing positions.

11. The calibration system of claim 1, wherein said calibration paddle comprises:

two to six calibration tiles.

12. The calibration system of claim 11, wherein said calibration tiles include one or more tiles selected from the group consisting of color reference tiles, trash reference tiles, and moisture reference tiles.

13. The calibration system of claim 1, wherein said calibration tiles include one or more tiles selected from the group consisting of color reference tiles, trash reference tiles, and moisture reference tiles.

14. The calibration system of claim 1, wherein said moving means comprises:

a shaft to which said calibration paddle is coupled; and a cylinder coupled to said shaft for laterally movement thereof.

15. The calibration system of claim 14, wherein said calibration paddle comprises:

two calibration tiles, and wherein said cylinder moves said shaft to sequentially position each calibration tile at its respective calibration location.

16. The calibration system of claim 14, further comprising:

control means coupled to said cylinder for controlling movement of said calibration paddle.

17. The calibration system of claim 16, further comprising:

a rotary actuator for moving said sampling device between the retracted position and the pressing position, wherein said control means is coupled to said rotary actuator for controlling movement of said sampling device.

18. The calibration system of claim 14, wherein said cylinder is a double-stroke air cylinder.

19. The calibration system of claim 14, further comprising:

a rotary actuator for moving said sampling device between the retracted position and the pressing position.

* * * * *